(12) United States Patent
Mills et al.

(10) Patent No.: US 7,621,740 B2
(45) Date of Patent: Nov. 24, 2009

(54) MAHONIA AQUIFOLIUM EXTRACT, EXTRACTION PROCESS AND PHARMACEUTICAL COMPOSITION CONTAINING THE SAME

(75) Inventors: Robert Mills, Toronto (CA); Rajiv Mathur, Ringoes, NJ (US); Nadya Lawrence, Cape May, NJ (US)

(73) Assignee: Prime Pharmaceutical Corporation, North York, Ontario (CA)

(*) Notice: Subject to any disclaimer, the term of this patent is extended or adjusted under 35 U.S.C. 154(b) by 0 days.

(21) Appl. No.: 11/682,602

(22) Filed: Mar. 6, 2007

(65) Prior Publication Data

US 2007/0148226 A1 Jun. 28, 2007

Related U.S. Application Data

(63) Continuation of application No. 10/669,416, filed on Sep. 25, 2003, now Pat. No. 7,205,006.

(51) Int. Cl.
A61K 36/00 (2006.01)
(52) U.S. Cl. ..................................... 425/725
(58) Field of Classification Search ............... None
See application file for complete search history.

(56) References Cited

U.S. PATENT DOCUMENTS

| | | | |
|---|---|---|---|
| 216,317 A * | 6/1879 | Du Rette ................. 424/765 |
| 3,882,244 A | 5/1975 | Lee |
| 4,054,589 A | 10/1977 | Bollag et al. |
| 4,105,681 A | 8/1978 | Bollag et al. |
| 4,215,215 A | 7/1980 | Bollag et al. |
| 4,356,167 A | 10/1982 | Kelly |
| 4,476,056 A | 10/1984 | Pawson |
| 4,713,394 A | 12/1987 | Thornfeldt |
| 4,818,533 A | 4/1989 | Boulware et al. |
| 4,866,048 A | 9/1989 | Calverley et al. |
| 5,292,727 A | 3/1994 | Godtfredsen |
| 5,595,743 A | 1/1997 | Wu |
| 5,607,693 A | 3/1997 | Bonte et al. |
| 5,849,776 A | 12/1998 | Czernielewski et al. |
| 5,856,487 A | 1/1999 | Upadhyay |
| 6,048,902 A | 4/2000 | Lebwohl et al. |
| 6,069,169 A | 5/2000 | Ptchelintsev |
| 6,210,680 B1 | 4/2001 | Jia |
| 6,238,696 B1 | 5/2001 | Wang |
| 6,254,896 B1 | 7/2001 | Davis |
| 6,271,001 B1 | 8/2001 | Clarke |
| 6,440,465 B1 | 8/2002 | Meisner |
| 2001/0000731 A1 | 5/2001 | Jia et al. |
| 2002/0164386 A1 | 11/2002 | Meisner |
| 2003/0096422 A1 | 5/2003 | Ong |
| 2003/0185915 A1 | 10/2003 | Carlo et al. |
| 2004/0043946 A1 | 3/2004 | Popp |
| 2004/0131706 A1 | 7/2004 | Rittinghausen et al. |
| 2005/0069576 A1 | 3/2005 | Mills et al. |

FOREIGN PATENT DOCUMENTS

| WO | WO 89/06537 | 7/1989 |
|---|---|---|
| WO | WO2005/027945 | 9/2003 |

OTHER PUBLICATIONS

Vollekova, A et al. 1: Phytother Res. Aug. 2003;17(7):834-7. Antifungal activity of Mahonia aquifolium extract and its major protoberberine alkaloids.*
Augustin, "Effects of Mahonia aquifolium ointment on the expression of adhesion, proliferation, and activation markers ub tge kin of patients with psoriasis," *Forsch Komplementarmed* 6(Suppl 2):19-21(1999).
Augustin, "*Mahonia aquifolium* in the treatment of psoriasis, a comparative study with dithranol", *Zeutschraft Phytotherapie*, 17:44-45 (1996).
Bernstein, et al, "Treatment of mild to moderate psoriasis with Relieva, a *Mohonia aquifolium* extract—A double-blind placebo-controlled study", *Amer. Journ. Therapeutics*, 13(2):121-126 (2006).
Bezakova, et al., "Lipoxygenase inhibition and antioxidant properties of protoberberine and aporphone alkanoids isolated from *Mahonia aquifolium*", *Pharmazie* 51(10):758-761 (1996).
Davidson and Diamond, "Autoimmune diseases", *N. Engl. J. Med.*, 345(5):340-50 (2001).
Gieler, et al., "*Mahonia aquifolium*—A new type of topical treatment for psoriasis", *J. Dermatol. Treatment*, 6(1):31-34 (1995).
Hajnicka et al, "Effect of *Mahonia aquifolium* active compounds on interleukin-8 production in the human monocytic cell line THP-1", *Planta Med.*, 68(3):266-8 (2002).
Konstantinova, et al., "Interleukin-8 is induced in skin equivalents and is highest in those derived from psoriatic fibroblasts", *J. Invest. Dermatol.*, 107(4):615-21 (1996).
Kuo, "The anti-inflammatory potential of berberine in vitro and in vivo", *Cancer Lett.*, 203(2)127-37 (2004).
Misik, et al., "Lipoxygenase inhibition and antioxidant properties of protoberberine and aporphine alkaloids isolated from *Mahonia aquifolium*", *Planta Med.*, 61(4)372-3 (1995).
Muller and Ziereis, "The antipsoriatic *Mahonia aquifolium* and its active constituents; I. Pro- and antioxidant properties and inhibition of 5-lipoxygenase", *Planta Med.*, 60(5):421-4 (1994).
Muller, et al., "The antipsoriatic *Mahonia aquifolium* and its active constituents; II. Antiproliferative activity against cell growth of human keratinocytes", *Planta Medica*, 61(1):74-75 (1995).
Nickoloff, et al., "Aberrant production of interleukin-8 and thrombospondin-1 by psoriatic keratinocytes mediates angiogenesis", *Am. J. Pathol.*, 144(4):820-8 (1994).

(Continued)

*Primary Examiner*—Michele C. Flood
(74) *Attorney, Agent, or Firm*—Pabst Patent Group LLP

(57) ABSTRACT

A skin treatment composition comprising a *Mahonia aquifolium* extract in a liposome delivery system is described. The *Mahonia aquifolium* extract is present in the skin treatment composition in a range of from 5% to 20% by weight of the total composition. The skin treatment composition is particularly effective in the treatment of psoriasis, eczema and other dry skin conditions. A process for obtaining an extract of *Mahonia aquifolium* is also disclosed.

4 Claims, No Drawings

OTHER PUBLICATIONS

Niedner, et al.,"Focus on Medication:Dermatology," *Deutsche Apotheker Zeitung* 37:10.09(1992).

Reichert, "Berberine and Psoriasis," *Quarterly Review Natural Medicine* 03(31):3-4(1997).

Schmeller, et al., "Biochemical activities of berberine, palmatine and sanguinarine mediating chemical defence against microorganisms and herbivores", *Phytochemistry,* 44(2):257-66 (1997).

Unger, "Improved detection of alkaloids in crude extracts applyinh capillary electrophoresis with field amplified sample injection" *J. Chrom.* 791:323-331 (1997).

Van De Kerkhof, et al., "Long-term efficacy and safety of tacalcitol ointment in patients with chronic plaque psoriasis", *British Journal of Dermatology,* 146(3):414-422 (2002).

Weisenauer, "*Mahonia aquifolium*—salbe bei Psoriasis vulgaris", *Z. Allg. Med.,* 16:23-31 (1992).

Weisenauer, "*Mahonia aquifolium* in patients with psoriasis vulgaris—as intraindividual study", *Phytomedicine,* 3(3):231-235 (1996).

X-Plain, "Psoriasis" Medline Plus, www.x-plain.com (2004).

* cited by examiner

MAHONIA AQUIFOLIUM EXTRACT, EXTRACTION PROCESS AND PHARMACEUTICAL COMPOSITION CONTAINING THE SAME

CROSS-REFERENCE TO RELATED APPLICATIONS

This is a continuation of U.S. Ser. No. 10/669,416 filed Sep. 25, 2003 entitled "*Mahonia Aquifolim* Extract, Extraction Process and Pharmaceutical Composition Containing the Same" by Robert Mills, Rajiv Mathur, and Nadya Lawrence. The disclosure in the application listed above is herein incorporated by reference, in its entirety.

FIELD OF THE INVENTION

The present invention is directed to a *Mahonia aquifolium* extract, a process for obtaining a concentrated form of the extract using a new extraction process and a pharmaceutical composition containing the extract. The pharmaceutical composition is a particularly effective treatment for psoriasis, eczema, dermatitis and other dry skin conditions.

BACKGROUND OF THE INVENTION

Psoriasis is a chronic skin disease that is characterized by scaling and inflammation of the skin. The scaling occurs when the cells in the outer layer of the skin reproduce faster than normal and pile up on the skin's surface. Psoriasis affects about 1.5% to 2% of the North American population. It occurs in all age groups and affects men and women equally. People affected by psoriasis suffer from discomfort, restricted joint motion and emotional distress. About 10% of people suffering from psoriasis have joint inflammation that produces symptoms similar to arthritis.

When psoriasis develops, patches of skin thicken, redden and become covered with silvery scales. These patches are generally referred to as plaques. The plaques are usually itchy and can burn. Psoriasis most often occurs on the elbows, knees, scalp, lower back, face, palms and soles of the feet.

A variety of treatments and methods have been used over the years including the topical application of corticosteroids, calcipotriene, coal tar, etc. Bath solutions and general moisturizers have been utilized by some patients. Sunlight and ultraviolet light treatments have also been used. In some instances systemic treatment using prescribed medicines taken internally are needed. Drugs taken internally include retinoids, methotrexate, hydroxyurea and antibiotics.

Each of these treatments has its benefits and drawbacks. In many instances, patients develop a tolerance to the treatment and the treatment becomes much less effective. The inventors have sought a treatment suitable for a variety of patients that overcomes the drawbacks noted above.

*Mahonia aquifolium* was originally found in the Pacific Northwest and British Columbia where it has been used for the treatment of psoriasis and eczema by Native North Americans for many centuries. It is an evergreen shrub that belongs to the Berberidaceae family.

The root and bark of the *Mahonia aquifolium* plant are known to contain isoquinoline alkaloids that include berberine, palmatine, berbamine, oxyacanthine, jatrorrhizine, bervulcine, magnoflorine and columbamine. These alkaloids are thought to be the active constituents of the plants as many of them have shown strong in vitro anti-microbial and anti-fungal activity.

*Mahonia aquifolium* may have several mechanisms of action in the treatment and management of psoriasis and other inflammatory conditions. Berberine and related alkaloids as noted above reversibly intercalate in DNA hindering replication and transcription. *Mahonia* extract contains isoquinoline alkaloids as outlined above. Isoquinoline has been identified as a component of coal tar which causes interfollicular regions of parakeratotic stratum corneum in mouse tail epidermis to become orthokeratotic, with concomitant production of a granular layer. In this respect, isoquinoline behaves similarly to coal tar and the isoquinolines may contribute to the anti-psoriatic activity of coal tar. Alkaloids isolated from the extract demonstrate anti-proliferation activity on keratinocytes. Hyper proliferation of keratinocytes is a major symptom of psoriasis and so controlling this activity will assist in the treatment of psoriasis. Lipoxygenase inhibition is strongly correlated with the lipid antioxidant effect of the protoberberine alkaloids, perhaps by reducing lipid hydroperoxide substrate accumulation. *Mahonia* is a moderate inhibitor of LTB-4 (a leukotriene which is believed to mediate inflammation) and 5-hydroxy-eicosatetraenoic acid (5-HETE) with an IC-50 in the same order of magnitude as anthralin. IC-50 refers to the concentration at which 50% inhibition occurs.

*Mahonia aquifolium* extract is also a very potent inhibitor of lipid peroxidation. Individual alkaloids isolated from the extract demonstrate anti-inflammatory activity by inhibiting the action of lipoxygenase. Oxidation products resulting from the action of lipoxygenase are known to be mediators of inflammation in other biological systems. The inhibitory effect of *Mahonia aquifolium* on lipid peroxidation contrasts with anthralin, which slightly stimulates lipid peroxidation. This difference may explain why *Mahonia aquifolium* extract reduces irritation.

DETAILED DESCRIPTION OF THE INVENTION

The *Mahonia aquifolium* extract of the present invention is obtained in a highly concentrated form using an extraction process as detailed below. The regents used in the extraction process are water, alcohol and crude dried *Mahonia aquifolium*.

The crude dried *Mahonia aquifolium* is obtained from dried bark and twigs of plants from the *Mahonia aquifolium* (Berberidaceae) family. Such plants include plants of the barberry family, for example, Oregon hollygrape.

The reagents are loaded into a stainless steel reactor vessel. The vessel is clamped shut. Pressure of 3 to 6 psi (volume dependent) is applied to the reactor vessel and the reagent mixture is heated to a temperature not higher than 50° C., preferably about 40° C., while mixing the contents with an internal counter-rotating agitating mixer. When the mixture reaches 40° C. an internal grinding mixer is engaged and the mixture is processed at a speed of about 3000 rpm (revolutions per minute) in combination with the internal counter-rotating mixer for three hours. The mixture is left under pressure of 3 to 6 psi in the reactor and is allowed to cool for not less than 24 hours.

After the 24 hours has elapsed the internal grinding mixer is again engaged and the mixture is processed at a speed of about 3000 rpm in combination with the internal counter-rotating mixer for three hours. The mixture is left under pressure of about 3 to 6 psi in the reactor for not less than 24 hours.

After the second 24 hour period, the internal grinding mixer is again engaged and the mixture is processed at a speed of about 3000 rpm in combination with the internal counter-rotating mixer for three hours. The mixture is then left under pressure of about 3 to 6 psi in the reactor for a minimum of 24 hours.

After the third 24 hour period, the pressure is released in the reactor and the reagent mixture is filtered through a coarse mesh filter and then through a 5 micron filter. The mixture is then placed under vacuum and heated to a minimum of 40° C. but not more than 50° C. while mixing to reduce and remove the solvents until the mixture is approximately 6% of its original volume. The resultant product is re-filtered through a 1-micron filter.

This extraction process yields a finished *Mahonia aquifolium* extract with a concentration of approximately 1.5 mg/ml berberine alkaloid. A typical alcohol based extraction process will yield a finished extract with a concentration of approximately 0.09 mg/ml berberine alkaloid.

The product obtained from this extraction process is then utilized to prepare a pharmaceutical composition suitable for use in the treatment of psoriasis and other skin ailments and diseases.

The pharmaceutical composition is prepared for use by combining the *Mahonia aquifolium* extract in a liposome delivery system.

Liposomes are microscopic spherical vesicles that form when phospholipids are hydrated. Recently, liposomes have been utilized and evaluated as delivery systems for drugs, vitamins and cosmetic materials. They can be custom designed for almost any use by varying the lipid content, size, surface charge and method of preparation. As the liposome wall is very similar, physiologically, to the material of cell membranes, they are particularly suitable for the delivery of products for application to the skin. When a pharmaceutical or cosmetic containing liposomes is applied to the skin, the liposomes are deposited on the skin and begin to merge with the cellular membranes. The liposomes release the active material into the cells and as a result the delivery of the active material is very specific. The liposome delivery system can be designed to release the active materials under a variety of conditions, for example, slow release, fast release, bilayer compositions, temperature dependent release, pH-dependent release, etc.

A preferred liposome delivery system for use in the pharmaceutical composition of the present invention is the Novasome® technology. Novasome lipid vesicles are comprised of molecules that possess both hydrophilic and hydrophobic properties (i.e. amphiphiles). The Novasome vesicles are made up of one or more lipid membranes or bilayers (generally 5 to 7) that surround a larger core. Each membrane is composed of amphiphiles in a bilayer array.

The core accounts for most of the vesicle volume, providing a high carrying capacity for water-soluble and water-immiscible substances. The Novasome bilayers are not in perfect array and contain vacancies (channels) through which encapsulated components can travel. Encapsulated components travel within and between each bilayer via a series of random jumps which causes lateral movement of the vacancies in the bilayer.

An active ingredient is contained in the core and can pass from the core through the bilayer. A sustained release mechanism is provided by the structure of the Novasome vesicles so a continuous and controlled release of the active ingredient can be achieved. As the active ingredient is entrapped within the core in a more protected manner prior to use the storage stability and the stability of the active ingredient is improved. This provides for more efficient and effective delivery of the active ingredient.

The pharmaceutical composition is prepared by combining *Mahonia aquifolium* extract in a concentration of approximately 5% to 20% by weight of the total composition in a liposome delivery system. The liposome delivery system detailed just above is one preferred delivery system. Preferred compositions have a concentration of *Mahonia aquifolium* of between 5% and 10% by weight of the total composition. This will provide the composition with a minimum of 0.712% berberine.

The remainder of the composition comprises typical pharmaceutically acceptable components, for example, diluents, adjuvants, etc.

The composition is utilized in a topical application form and is applied directly to the affected area. The composition can be in the form of a lotion or cream.

Three typical formulations are detailed below. The percent by weight noted of each component is a percent by weight of the total composition. The *Mahonia aquifolium* extract is in the liposome delivery system.

| Component | percent by weight |
|---|---|
| Lotion | |
| DI water | 51.04 |
| Mahonia extract | 10.00 |
| transcutol | 8.00 |
| glyceryl dilaurate | 8.00 |
| glyceryl monostearate | 4.50 |
| 96% glycerin | 3.41 |
| diisopropyl adipate | 3.00 |
| cyclomethicone | 2.50 |
| dimethicone | 2.00 |
| octyl palmitate | 1.40 |
| $C_{12-15}$ alcohol lactate | 1.00 |
| chamomile extract | 1.00 |
| stearoxydimethicone | 0.70 |
| cholesterol | 0.50 |
| Polysorbate 80 ™ | 0.50 |
| cetearyl glucoside | 0.50 |
| cetyl alcohol | 0.50 |
| green tea extract | 0.50 |
| phenoxyethanol | 0.40 |
| Methylparaben ™ | 0.20 |
| xanthan gum | 0.15 |
| disodium EDTA | 0.10 |
| vitamin E acetate | 0.10 |
| Cream | |
| DI water | 44.95 |
| Mahonia extract | 10.00 |
| transcutol | 10.00 |
| glyceryl dilaurate | 8.00 |
| glyceryl monostearate | 4.50 |
| 96% glycerin | 3.41 |
| cyclomethicone | 3.00 |
| dimethicone | 2.50 |
| cetearyl glucoside | 1.50 |
| PEG-150 monstearate | 1.50 |
| diisopropyl adipate | 1.50 |
| stearoxydimethicone | 1.00 |
| $C_{12-15}$ alcohol lactate | 1.00 |
| ethyl oleate | 1.00 |
| diisopropyl sebacate | 1.00 |
| cetyl alcohol | 1.00 |
| chamomile extract | 1.00 |
| Sepigel 305 ™ | 1.00 |
| green tea extract | 0.50 |
| cholesterol | 0.50 |
| phenoxyethanol | 0.40 |
| xanthan gum | 0.30 |
| Methylparaben | 0.20 |
| disodium EDTA | 0.10 |
| alpha toccopherol acetate | 0.10 |
| citric acid | 0.04 |

-continued

| Component | percent by weight |
|---|---|
| Scalp Therapy Composition | |
| DI water | 67.34 |
| Mahonia extract | 10.00 |
| glyceryl monostearate | 4.50 |
| chamomile extract | 3.00 |
| propylene glycol | 2.50 |
| avocado unsaponifiable | 2.00 |
| Quaterium 22 ™ | 2.00 |
| cyclomethicone | 1.40 |
| behentrimonium methosulfate | 1.00 |
| cetearyl alcohol | 1.00 |
| aloe vera powder | 1.00 |
| green tea extract | 1.00 |
| wheat germ oil | 1.00 |
| stearyl alcohol | 0.70 |
| triethanolamine | 0.66 |
| Quaterium 26 ™ | 0.50 |
| Methylparaben | 0.20 |
| DMDM hydantoin | 0.20 |

In clinical studies and trials, as detailed below, the beneficial effects of the composition of the present invention were noted.

In one trial psoriatic patients having mild to moderate psoriasis applied the composition of the present invention to one half of the affected area. To the other side of the affected area the patients applied a plain vehicle cream (the cream utilized to prepare the composition of the present invention). The compositions were applied twice a day for four weeks. All eleven patients were compliant and finished the four week course of the study. Nine patients improved, one remained the same throughout the treatment but was less pruritic and one improved on the plain vehicle cream side only. Of the nine patients that improved, one patient cleared on both sides, one patient improved on both sides equally, one patient improved slightly on the side utilizing the composition of the present invention and six patients were definitely improved on the side utilizing the composition of the present invention.

In another study low concentrations of *Mahonia aquifolium* extract in a cream base demonstrated that the preparation was safe and well tolerated when applied to plaques of psoriasis.

A second study was initiated to examine the safety, tolerability and efficacy of higher concentrations of *Mahonia aquifolium* extract in 33 patients with a variety of types of psoriasis and 8 patients with eczema. The study was an observational study.

The patient population included a wide range of age groups and included both sexes. Treatments prior to the start of the application of *Mahonia aquifolium* extract ranged from no treatment to topical corticosteroids, Dovonex™, ultraviolet light and methotrexate.

*Mahonia* extract and vehicle treated lesions were photographed prior to treatment and throughout the study. The target lesions were scored for scaling, thickness and redness. In almost all cases scaling was the first symptom to improve. In many cases improvement was noted after the first week of treatment. The thickness of the plaques generally declined substantially over 2 to 4 weeks. Redness improved most gradually. This is common for most psoriasis treatments.

In some cases the methotrexate and/or ultraviolet light treatment continued when the application of *Mahonia* extract started. The *Mahonia* extract did not cause any adverse interactions with these treatments and there was no evidence of photosensitivity or phototoxicity. *Mahonia* cream may be a complementary treatment. There was no clinical evidence that the creams being tested blocked or interfered with ultraviolet light.

The *Mahonia* cream was enthusiastically accepted by all the patients and compliance with and adherence to the experimental protocol was good. In all cases of both psoriasis and eczema the side treated with *Mahonia* cream did as well as or better than the side treated with the vehicle cream alone.

The invention claimed is:

1. A process for obtaining an extract of *Mahonia aquifolium* comprising the steps of: (a) applying heat and pressure to a stirred mixture of water, alcohol and crude dried *Mahonia aquifolium*, to heat the mixture to a temperature not higher than 50° C., and to a pressure between 3 and 6 psi; (b) processing the mixture with a grinder at a speed about 3000 rpm for about three hours; (c) allowing the mixture to cool under pressure for at least 24 hours; (d) repeating the last two steps at least twice more; (e) releasing the pressure and filtering the mixture to obtain a filtrate; (f) placing the filtrate under vacuum and heating the filtrate to a temperature not higher than 50° C. while stirring to reduce and remove the alcohol and water until the filtrate is approximately 6% of its original volume to obtain a heated filtrate; and (g) filtering the heated filtrate though a 5 micron filter to obtain the extract of *Mahonia aquifolium*.

2. The process of claim 1 wherein the extract is filtered through a one micron filter.

3. The process of claim 1 wherein in step (a) the mixture is heated to a temperature of 40° C.

4. The process of claim 1 further comprising placing the extract in a liposome delivery system.

* * * * *